United States Patent [19]

Nürnberg et al.

[11] Patent Number: 5,766,628
[45] Date of Patent: Jun. 16, 1998

[54] BATH AND SHOWER COMPOSITION HAVING VESICLE-FORMING PROPERTIES AND METHOD FOR THE PRODUCTION AND USE THEREOF

[75] Inventors: Eberhard Nürnberg, Uttenreuth; Thomas Gassenmeier, Nürnberg; Rolf Dieter Beutler, Höchst/Odenwald; Jürgen Ebinger, Hünstetten, all of Germany

[73] Assignee: Merz + Co. GmbH & Co., Frankfurt, Germany

[21] Appl. No.: 852,038

[22] Filed: May 6, 1997

Related U.S. Application Data

[63] Continuation of Ser. No. 458,021, Jun. 1, 1995, abandoned, which is a continuation of Ser. No. 148,950, Nov. 8, 1993, abandoned, which is a continuation-in-part of Ser. No. 941,398, Sep. 8, 1992, abandoned.

[30] Foreign Application Priority Data

Feb. 24, 1992 [DE] Germany .......................... 42 05 548.2

[51] Int. Cl.⁶ .............................. A61K 31/00; A61K 7/00
[52] U.S. Cl. .................................. 424/450; 424/70.31
[58] Field of Search ............................ 424/450, 70.31

[56] References Cited

U.S. PATENT DOCUMENTS

| | | | |
|---|---|---|---|
| 5,004,611 | 4/1991 | Leigh | 424/450 |
| 5,075,113 | 12/1991 | Du Bois | 424/450 |
| 5,089,268 | 2/1992 | Katz | 424/450 |
| 5,098,606 | 3/1992 | Nakajima | 424/450 |
| 5,149,860 | 9/1992 | Zysman | 560/160 |

OTHER PUBLICATIONS

Hauser, H., Chimia 39, 252–264 (1985).

New, R.R.C., "Liposomes—A Practical Approach", Oxford University Press, 1990, Cover Sheet, Table of Contents, pp. 36–74, 98–100.

*Primary Examiner*—Sally Gardner-Lane
*Attorney, Agent, or Firm*—The Firm of Gordon W. Hueschen

[57] ABSTRACT

The invention relates to novel essentially anhydrous oily bath and shower compositions containing a combination of fatty oil and/or fatty or waxy apolar substance, oil-soluble surfactant, and vesicle-forming lipid and, if desired, a cosmetically- or balneologically-active ingredient. When poured into or simply admixed with water, these formulations immediately and automatically, generate dispersed vesicles or liposomes. They exhibit an immediate as well as a prolonged or depot effect, can be used alone or added to or together with existing bath or shower formulations, and are especially suited for use in connection with or as additives to full, partial, or shower baths.

18 Claims, 2 Drawing Sheets

BATH AND SHOWER COMPOSITION HAVING VESICLE-FORMING PROPERTIES AND METHOD FOR THE PRODUCTION AND USE THEREOF

The present invention is a continuation of our prior-filed application Ser. No. 08/458,021, filed Jun. 1, 1995, which is in turn a continuation of our prior-filed application Ser. No. 08/148,950, filed Nov. 8, 1993, which is in turn a continuation-in-part of our prior-filed application Ser. No. 07/941,398, filed Sep. 8, 1992, all of which prior applications are now abandoned.

FIELD OF INVENTION

Bath and shower additives, e.g., bath oils and the like.

The present invention relates to new and essentially anhydrous bath and shower additives comprising a combination of a fatty oil or other fatty apolar substance, an oil-soluble surfactant, a vesicle-forming lipid, and other active ingredients as desired or required. When poured and/or admixed into water to produce the bath or shower water, liquid, or liquor, these compositions spontaneously i.e., automatically and immediately, form dispersed vesicles or liposomes. They are especially suitable for use as or in the production of long-acting, depot, or extended-action additives for full, partial, and shower baths.

By the term "vesicle", as used herein, is intended a small bladder or enclosed membrane filled with fluid, for all intents and purposes being equivalent to a liposome, as is well understood by one skilled in the art, vesicles or liposomes being generally globular units consisting of concentric bi-layers which may be, depending upon the size and number of possibly superposed bi-layers, unilamellar, oligolamellar, or multilamellar by nature, and which in the present case are probably what are commonly known as "reverse micelles", having exterior bilayers of lipidic or other apolar material, capable of solubilizing water and any contained cosmetically-active ingredient in the polar center thereof.

BACKGROUND OF THE INVENTION AND PRIOR ART

For balneological (viz., the therapeutic use of baths) and/or sanitary or cosmetic purposes, various formulations containing surfactants are commonly employed. These contain, for example, surfactants which are miscible with or dispersible in water and, if required, perfumes and additional active ingredients such as essential oils, herbal extracts, vitamins, and the like. Such preparations are based essentially on ionic or non-ionic surfactants and the above-mentioned active ingredients, which—after being added to water-ensure a uniform dispersion of the components. The preparations are either clear or exhibit a more or less pronounced opalescence. The bath liquor embodying such preparations is usually clear or slightly turbid.

In addition to such products, oily balneological, sanitary, and/or cosmetic preparations are known. These products are distinguished from the foregoing preparations by the relatively high percentage of fatty oils or other lipophilic liquids contained therein in addition to the tenside, i.e., the surface-active agent. In contrast to essentially oil-free products, these oily preparations produce turbid bath waters, liquids, or liquors in which the lipophilic constituents are at first dispersed relatively uniformly. After ten to thirty minutes, there is an increased flotation to the surface. Extent and rate of this so-called "creaming" process depend inter alia upon various factors such as type and quantity of the contained surfactant and/or dispersion agent, type and quantity of the lipophilic agent, and water temperature.

In addition to the aforementioned products, there are also balneological preparations containing only a fatty oil—if required or desired in addition to other oily components— and possibly other active ingredients such as essential oils. Inasmuch as these products, after being added to the water, develop unsatisfactory dispersibility of the lipophilic constituents, forming a more or less uniform layer thereof on the bath liquor surface in the absence of surfactant, they are relatively unsuited for balneological applications. To achieve a satisfactory balneological and/or cosmetic effect, dispersion agents or surfactants are required for dispersing the oils in the bath water. This ensures deposit of a uniform dispersion of the oil phase on the skin surface. Moreover, in addition, penetration of the active ingredients contained in the preparation into the deeper skin layers should preferably be enhanced to achieve a potentiation of their effect. However, due to an absence of vesicular properties in such prior art compositions, this has so far not been possible with known formulations. But, according to the present invention, dispersed vesicles or liposomes are formed spontaneously and substantially automatically and immediately upon admixture of a composition of the invention with the bath or shower water.

During prosecution of the parent application, considerable art prior has been called to the attention of the Examiner since previously, as already disclosed in this Specification itself, and as further disclosed in the numerous documents provided to the Examiner, only complex procedure for the formation of vesicles or liposomes was available and, in fact, in the major Reference A cited during prosecution of the parent application, namely, Zysman, which produced only formulations containing huge percentages of water, vigorous shaking "for a period ranging from 15 minutes to 3 hours approximately" was required to effect mixing and obtain vesicle formation. Such a time period for the production of vesicles or liposomes is simply too long for the present applicants' intended purpose and use in shower or bath, for which purpose spontaneous, i.e., essentially instantaneous and automatic upon simple admixture with the bath or shower liquid, vesicle or liposome formation is required, as fully set forth throughout this Specification. The 15 minutes to 3 hour time period required for vesicle formation according to the Zysman reference, namely, U.S. Pat. No. 5,149,860, issued Sep. 22, 1992, is a sufficiently long period of shaking so that most people will have been into and out of the shower or bath several times by the time the vesicles or liposomes are produced and, accordingly, such a reference and the procedure of such a reference is totally irrelevant and unsuited as far as the objectives and intended purpose and use of the present invention. Moreover, the compositions of the invention are essentially anhydrous and contain only those small vestiges of water which may be present in the individual ingredients, since an object of the present invention is to provide essentially anhydrous compositions which spontaneously, i.e., automatically or instantaneously, form dispersed vesicles or liposomes upon simply being poured into or admixed with bath or shower water, and the presence of any substantial amount of water in a composition of the invention would accordingly be destabilizing and reduce such desired spontaneous effectiveness.

OBJECTS OF THE INVENTION

An objective of the present invention, therefore, is to provide a balneological or cosmetic bath additive which— when used for bathing or showering—provides and releases dispersed vesicles or liposomes spontaneously, i.e., essentially automatically and instantaneously, without the necessity of expensive procedures for their production. In consequence, the additive of the invention has not only a surface-active effect, but also sets free the incorporated ingredients and components in a sustained release form, i.e., in the form of vesicles, thereby considerably improving the duration of the balneological or cosmetic effect. Other objects of the invention will become apparent hereinafter, and still others will be obvious to one skilled in the art.

SUMMARY OF THE INVENTION

The invention, then, comprises the following, inter alia, singly or in combination:

an essentially anhydrous balneological or cosmetic composition suitable as an additive for use in bathing or showering, having vesicle-forming properties, which is capable of spontaneous dispersed liposome or vesicle formation upon being admixed with water consisting essentially of a fatty oil and/or a fatty or waxy apolar substance, one or more oil-soluble surfactants, an optional cosmetically-active ingredient, and one or more vesicle-forming lipids, the said composition containing 20% to 90% fatty oil and/or apolar substance, 2% to 50% oil-soluble surfactant, and 0.1% to 20% vesicle-forming lipid, all by weight of total composition; such a composition wherein the vesicle-forming lipid has an HLB value of about 2 to about 6 or is a phospholipid; such a composition wherein the percentage of fatty oil and/or apolar substance is 50% to 70%, the percentage of oil-soluble surfactant is 5% to 35%, and the percentage of vesicle-forming lipid is 0.5% to 5%, all by weight of total composition; such a composition wherein the percentage of oil-soluble surfactant is 10% to 20% by weight; such a composition wherein the fatty oil or apolar substance is selected from the group consisting of peanut, sesame, sunflower, wheat germ, soy, jojoba, castor, almond, mink, and olive oils and mixtures thereof as fatty oil, and paraffin oil, isopropyl myristate, isopropyl palmitate, medium-chain triglycerides, isooctyl stearate, capryl/capric acid triglycerides, cetyl palmitate, and mixtures thereof as apolar substance; such a composition wherein the oil-soluble surfactant is an oil-soluble, water-dispersible tenside having an HLB value of 6 to 13; such a composition wherein the HLB value is 7 to 10; such a composition wherein the oil-soluble surfactant is selected from the group consisting of polyoxyethylene lauryl ether having 1 to 4 EO units, polyoxyethylene(5)-oleyl ether, polyoxyethylene(7)glyceryl cocoate, cocoa fatty acid diethanolamide, ethanolamide, mono or di or tri (alkyl tetraglycol ether)-ortho-phosphoric acid esters, polyoxyethylene glycerol trioleate, polyoxyethylene sorbitan tristearate, polyoxypropylene(15)-stearyl ether, and mixtures thereof; such a composition wherein the vesicle-forming lipid is selected from the group consisting of a lower polyoxyethylated fatty alcohol having an HLB value between 2 and 6 and a phospholipid; such a composition wherein the fatty alcohol is a higher polyoxyethylated fatty alcohol having 1 to 4 ethylene oxide units, and the phospholipid is lecithin, phosphatidylcholine, -serine, or -diethanolamine, or a mixture thereof; such a composition wherein the polyoxyethylated fatty alcohol is based upon a $C_{16}$–$C_{18}$ alcohol; such a composition containing up to about 30% of cosmetically-active ingredient; such a composition containing 5 to 15% active ingredient; such a composition wherein the active ingredient is selected from the group consisting of essential oils, herbal extracts, and vitamins; such a composition additionally containing up to about 10% thickener; such a composition wherein the thickener is selected from aerosil and aluminum or magnesium stearate; such a composition incorporated into a bath or shower formulation; and such a composition wherein the oil and/or apolar component is selected from the group consisting of soya oil, paraffin oil, isopropyl myristate, jojoba oil, isopropyl palmitate, capric acid triglyceride, and mixtures thereof, wherein the oil-soluble surfactant is selected from the group consisting of alkyl tetraglycol ethers, polyoxyethylene (7)glycerol cocoate and coconut oil diethanolamide, and wherein the vesicle-forming lipid is lecithin.

Moreover, a method for the production of an essentially anhydrous bath or shower additive composition, which is capable of dispersed liposome or vesicle formation spontaneously upon being admixed with water, wherein 20% to 90% fatty oil and/or fatty or waxy apolar substance, 0% to 30% cosmetically-active ingredient, 2% to 50% of one or more oil-soluble surfactants, and 0.1% to 20% of one or more vesicle-forming lipids, are admixed together as essential ingredients at a temperature between about 20° C. and 70° C; such a method wherein the vesicle-forming lipid has an HLB value of about 2 to about 6 or is a phospholipid; such a method wherein the amount of fatty oil and/or apolar component is 50% to 70%, the amount of active ingredient is 5% to 15%, the amount of surfactant is 10% to 20%, and the amount of vesicle-forming lipid is 0.5% to 5%; such a method wherein up to about 10% by weight of thickener, based upon the total weight of ingredients, is included in the composition; such a method wherein the thickener is selected from aerosil and aluminum or magnesium stearate; such a method wherein the fatty oil or apolar substance is selected from the group consisting of peanut, sesame, sunflower, wheat germ, soy, jojoba, castor, almond, mink, and olive oils and mixtures thereof as fatty oil, and paraffin oil, isopropyl myristate, isopropyl palmitate, medium-chain triglycerides, isooctyl stearate, capryl/capric acid triglycerides, cetyl palmitate, and mixtures thereof as apolar substance; such a method wherein the oil-soluble surfactant is an oil-soluble, water-dispersible tenside having an HLB value of about 6 to about 13, and especially between about 7 and about 10; such a method wherein the oil-soluble surfactant is selected from the group consisting of polyoxyethylene lauryl ether having 1 to 4 EO units, polyoxyethylene(5)oleyl ether, polyoxyethylene(7)glyceryl cocoate, cocoa fatty acid diethanolamide, ethanolamide, mono or di or tri (alkyl tetraglycol ether)-ortho-phosphoric acid esters, polyoxyethylene glycerol trioleate, polyoxyethylene sorbitan tristearate, polyoxypropylene(15)-stearyl ether, and mixtures thereof; such a method wherein the vesicle-forming lipid is selected from the group consisting of a lower polyoxyethylated fatty alcohol having an HLB value between 2 and 6 and a phospholipid; such a method wherein the fatty alcohol is a higher polyoxyethylated fatty alcohol having 1 to 4 ethylene oxide units, and the phospholipid is lecithin, phosphatidylcholine, -serine, or -diethanolamine, or a mixture thereof; such a method wherein the polyoxyethylated fatty alcohol is based upon a $C_{16}$–$C_{18}$ alcohol; such a method wherein up to about 30% of active ingredient, selected from the group consisting of essential oils, herbal extracts, and vitamins, is included in the composition; and finally such a method wherein the oil and/or apolar component is selected from the group consisting of soya oil, paraffin oil, isopropyl myristate, jojoba oil, isopropyl palmitate, capric acid triglyceride, and mixtures thereof, wherein the oil-soluble surfactant is selected from the group consisting of alkyl tetraglycol ethers, polyoxyethylene (7)glycerol cocoate and coconut oil diethanolamide, and wherein the vesicle-forming lipid is lecithin.

GENERAL DESCRIPTION OF THE INVENTION

According to the present invention, the problem is solved by the provision of essentially anhydrous bath or shower additives containing a fatty oil and/or other apolar fatty substance and, if required, an active ingredient and, in addition, a combination of an oil-soluble surfactant and a vesicle-forming lipid.

Such combinations are unexpectedly characterized in that, when poured into or admixed with bath or shower water, they spontaneously, i.e., automatically or instantaneously, form vesicles, although it is known that special methods and equipment are usually required to produce them. Previous processes are characterized in that lamellar units must first be produced which—by applying high-energy techniques such as ultrasound, high-pressure jet, or high-speed agitators—must then be converted into globules having a small particle size.

It was therefore most surprising (a) that the formulations according to the invention in or with water form vesicles, although—as described above—vesicles are usually formed only by applying high external energy, and moreover (b) that the vesicle-forming constituents incorporated into the bath water are not dissolved. However, the vesicles are in fact formed in the bath water and accordingly greatly enhance the value of the compositions of the present invention as compared to similar prior art products.

The vesicles obtained according to the invention are globular units consisting of concentric bi-layers. Depending on the size and the number of possibly superposed bi-layers, distinction is made between unilamellar and multilamellar or oligolamellar vesicles. These surfactant associates, namely, the vesicles, are characterized by considerable stability and anisotropy (viz., determinable and reproducible regularly-variable properties) and can frequently be seen under the polarization microscope. Therefore, the presence of such vesicles, and particularly the multilamellar vesicles, can be established by use of a polarization microscope. In contrast to many vesicles produced previously, the vesicles produced according to the present invention do not require the presence of a stabilizer such as cholesterol.

By employment of the new additives of the present invention, the balneological and/or cosmetic effect of bath formulations can be considerably potentiated, because the active ingredients are thus able to act via the liposomes or vesicles over an extended period on and in the skin, inasmuch as the oily component serves as an action vehicle and depositing system for the active ingredients which are then set free in a sustained release manner. Therefore, the effect of the oil baths attained by employment of a formulation according to the invention goes beyond the temporary and short-term care so far achievable, as lipo- somes and vesicles are known to exert a favorable effect on the epidermis in the sense of a depot effect of lipids and active ingredients, thereby inter alia positively influenc- ing the hydration capacity of the skin over an extended time period.

Oil Component

The oil bath formulations according to the invention may contain common fatty oil components and preferably an oil selected from the group consisting of peanut, sesame, sunflower, soy, jojoba, castor, almond, olive, mink and wheat germ oils, and mixtures thereof.

As apolar substance (by which is meant a non-polar substance), which may be employed together with or instead of the fatty oil according to the present invention, may be mentioned all kinds of non-polar materials of an oily, fatty, or waxy nature, as set forth in the following. Thus, other suitable components of the oil phase can accordingly be fatty or waxy apolar substances such as paraffin hydrocarbons, esters of higher alcohols and higher fatty acids (so-called wax esters), and higher fatty alcohols. Representative preferred components are:

Paraffin oil

Isopropyl myristate

Isopropyl palmitate

Medium-chain length triglycerides

Propylene glycol esters of medium-chain length fatty acids

2-Octyl dodecanol

Hexyl dodecanoate

Isooctyl stearate

Capryl/capric acid triglyceride

Cetyl palmitate, and the like.

Such substances, which are already used for incorporation into oil bath compositions, can be used individually or in combination with the above-described oil components or mixtures thereof.

Especially preferred are soy, paraffin, and jojoba oils, as well as isopropyl myristate, isopropyl palmitate, and capric acid triglyceride, and mixtures thereof.

Oil-Soluble Surfactant

The surfactant employed according to the present invention is a fat- or oil-soluble surfactant or tenside, such as sorbitan monooleate, docusate sodium, or the like, which is capable of inducing formation of the vesicles or liposomes which are essential according to the present invention. As oil-soluble tensides for the dispersion of the oil phase, common surfactants can therefore be used. These comprise oil-soluble, water-dispersible substances, especially those having HLB values between about 6 and 13, and preferably between about 7 and 10. Particularly preferred are the following surface-active substances:

Polyoxyethylene lauryl ether with 1 to 4 EO units of medium chain length

Polyoxyethylene (5) oleyl ether

Polyoxyethylene (7) glyceryl cocoate

Coconut acid diethanolamide

Mono-, di-, and tri-(alkyl tetraglycol ether) orthophosphoric acid esters (mixture)

Polyoxyethylene glycerol trioleate

Polyoxyethylene sorbitan tristearate

Polyoxypropylene (15) stearyl ether, and the like.

Especially preferred are polyoxyethylene lauryl ether with 1 to 4 EO units, polyoxyethylene (7) glycerol cocoate, coconut acid diethanolamide, and mixtures thereof.

Vesicle-Forming Lipid

As vesicle-forming lipid, known substances may be employed, such as polyoxyethylated fatty alcohols with preferably 1 to 4 EO in an HLB range from about 2 to 6, the lipophilic group preferably comprising a $C_{16}$–$C_{18}$ fatty alcohol.

Higher analogues of the respective fatty acids and phospholipids are also suitable, especially such as lecithin (egg or soy lecithin), phosphatidylcholine, -serine, or -diethanolamine, and mixtures thereof.

Other suitable lipidic components utilizable for the production of vesicles or mixed vesicles include sphingo lipids (e.g., sphingosine, ceramides, cerebrosides, sphingomyelin), cholesterol, quaternary ammonium compounds, polyglycerol alkyl ethers, glucosyl dialkyl ethers, saccharose diesters, sulfuric acid esters of higher alcohols, collagen hydrolysate esters, bile acids, and poloxamers.

Such compounds are already known for the production of liposomes (cf. DE 41 21 945.7). However, in that case the vesicles were produced and incorporated into the desired preparations only by expensive procedure and usually required a stabilizer, neither of which are required according to the present invention.

Active Ingredient

As described, the formulations according to the invention can contain 0 to 30%, preferably 5 to 15%, of one or more active ingredients such as essential oils, herbal extracts, and/or vitamins in usual amounts. These active ingredients may representatively comprise Oleum menthae japonicum, rosemary oil, lavender oil, menthol, as well as jojoba oil, linden blossom, calendula, panthenol, Aloe vera extract, vitamin E, avocado oil, ivy extract, eucalyptus oil, thyme oil, a phyto lipid, or the like. Depending upon the effect desired, such as improvement of skin structure, care of sensitive skin, stimulation of circulation, or relaxation, a suitable combination of active ingredients can be employed. If required, traditional auxiliary agents can be added in usual amounts (e.g., 1–10%) such as thickening or jellifying agents, e.g., aerosil, aluminum or magnesium stearate or analogues thereof, and mixtures thereof, depending upon the exact type of product desired and the effect intended to be attained.

Especially suited for the vesicle-forming compositions of the present invention are combinations containing 20 to 90% oil component (fatty oil and/or fatty or waxy apolar substance), 2 to 50% of oil-soluble surfactant or mixtures thereof, 0.5 to 5% of lipid and, if desired, 5 to 15% of one or more active ingredients.

When introduced into water, the formulations according to the invention produce both an immediate and a depot effect. Based upon the composition of the formulations according to the invention, this two-phase action in the water effects both a considerable increase in and prolongation of the intended effect, or a liposome-based cosmetic depot and "caring" effect without the necessity of additional effort in either the production or application, i.e., use, of the preparation.

In addition, the compositions or formulations according to the invention ensure a uniform dispersion of the oil phase in the bath water. Although vesicle-forming lipids themselves possess some degree of emulsifying effect, they are normally unable to ensure sufficient dispersion in the bath water of all of the oil present in the composition. The formulations according to the invention may therefore contain less lipophilic surfactants and/or reduced amounts thereof, and therefore have a balancing effect in this regard. It is only due to a resulting uniform distribution and dispersion that vesicles can be formed. Therefore, on the one hand, the formulations according to the invention are characterized by their high capacity for emulsification of the oil phase in the bath liquor and, on the other hand, by their capacity for spontaneous, i.e., automatic or instantaneous, vesicle formation. Both of these aspects and both the tenside and the lipidic components are essential for the production of the products according to the invention, thereby generally leading to highly-desirable transparent compositions.

BRIEF DESCRIPTION OF THE DRAWINGS

Referring now to the drawings.

SPECIFIC DESCRIPTION OF THE INVENTION

Figure 1:
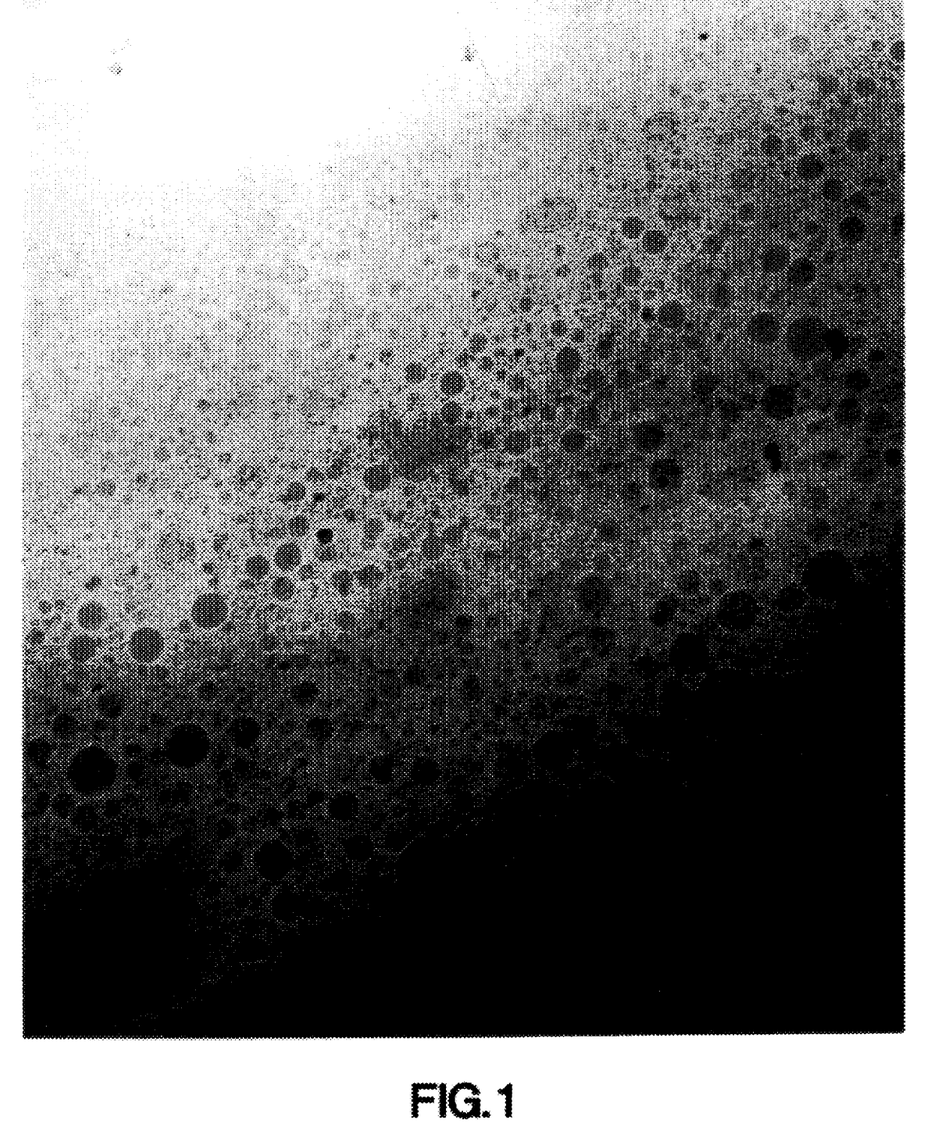
FIG. 1 is an enlarged view of a product according to the present invention as produced according to Example 1 hereof, showing the vesicular components thereof in the form of multiple circles as seen under an electron microscope.
Figure 2:
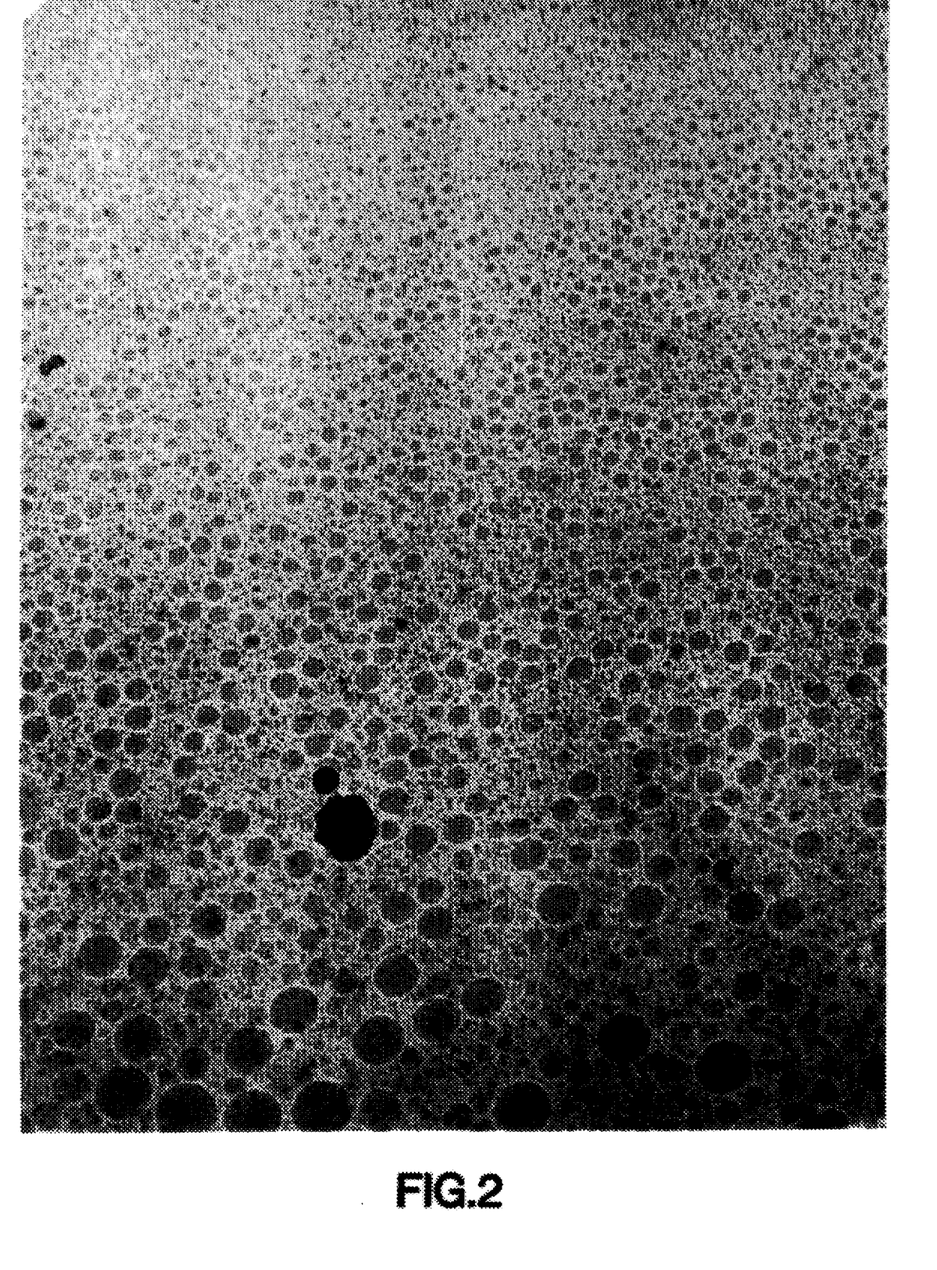
FIG. 2 is a view of a conventional bath oil formulation containing the bath oil plus surfactant without vesicle-forming lipid, as seen under an electron microscope, evidencing the absence of vesicles, only single circles and no double circles characteristic of bilayer vesicles being apparent.

Formulations according to the invention are produced by traditional methods using traditional equipment (stainless steel vessel with agitator). Into this vessel the essentially anhydrous individual components are introduced, mixed, and formulated into a finished product. Depending upon the type of product desired (e.g., for bath or shower bath), innumerable suitable and common auxiliary agents can be included therein. The invention is described in more detail by the following examples, which are given to illustrate the composition and method of the present invention but which are not to be construed as limiting. As can be seen, in each case the stated ingredients make up 100% of the composition, i.e., are essentially anhydrous and contain only those small vestiges of water which may be present in the individual ingredients, since an object of the present invention is to provide essentially anhydrous compositions which spontaneously, i.e., automatically or instantaneously, form dispersed vesicles or liposomes upon simply being poured into or admixed with bath or shower water, and the presence of any substantial amount of water in a composition of the invention would accordingly be destabilizing and reduce such desired spontaneous effectiveness.

EXAMPLE 1

Preparation of an oil bath preparation

Introduce soy oil and paraffin oil into a stainless steel vessel with agitator. Add, under stirring, Laureth-4 and the following essentially anhydrous components in the order described. Prepare the product within a temperature range between 20° and 70° C. Subsequently cool, filter (100 µm), portion, and package.

| Composition 1 | |
|---|---|
| Soy oil | 50% |
| Paraffin oil | 20% |
| Laureth-4 (CTFA - ethoxylated lauryl alcohol-surfactant) | 15% |
| Coconut acid diethanolamide | 5% |
| Lecithin | 3% |
| Eucalyptus oil | 4% |
| Pine oil | 2.5% |
| Tocopherol acetate | 0.5% |

EXAMPLE 2

The following bath formulation was prepared in the manner described in Example 1.

| Composition 2 | |
|---|---|
| Soy oil | 30% |
| Isopropyl myristate | 20% |
| Octyl dodecanol | 20% |
| Jojoba oil | 5% |
| Mono/di/tri (alkyltetraglycol ether)/o/phosphoric acid ester | 5% |
| Polyoxyethylene (7) glycerol cocoate | 5% |
| Lecithin | 5% |
| Ivy extract | 5% |
| Panthenol (B-complex Vitamin) | 3% |
| Perfume oil | 2% |

EXAMPLE 3

A shower gel preparation was prepared according to the foregoing procedure.

| Composition 3 | |
|---|---|
| Soy oil | 36% |
| Paraffin oil | 20% |
| Laureth-3 (CTFA - ethoxylated lauryl alcohol-surfactant) | 10% |
| Polyoxyethylene (7) glyceryl cocoate | 10% |
| Capryl/capric acid triglyceride | 10% |
| Isopropyl palmitate | 8% |
| Sphingosine | 1% |
| Eucalyptus oil | 1% |
| Aerosil (finely-divided SiO$_2$ thixotropic agent) | 3% |
| Perfume oil | 1% |

Clinical Evaluation

The increased efficacy of the products according to the present invention was demonstrated in clinical trials. In these studies, two galenical formulations according to the present invention were tested on human volunteers.

Test 1

A product according to the invention containing 70% of oil/apolar substances, 20% of surfactants, 3% of lecithin, as well as eucalyptus oil, pine oil and thyme oil as active ingredients (composition as per Example 1), was tested as follows:

Objective

To determine whether and to what extent the microcirculation in the skin can be improved by the new two-phase bath formulation, which produces spontaneous, i.e., automatic and instantaneous, formation of vesicular lipid particles containing active ingredients dispersed in the bath water upon being poured into or by simple admixture with the same.

Ten volunteers with healthy skin were included in the study. The trial was carried out using a common dosage of 30 grams of bath concentrate per 100 liter of water at a temperature of 37° C.

For objective comparison, the same measurements were made using blank water.

The following methods were applied to determine the cutaneous microcirculation:

Laser Doppler measurement of erythrocyte flux

Measurement of partial transcutaneous oxygen pressure

Measurement of skin temperature

Results

In healthy skin, the product according to the invention, as compared to blank water, effects an immediate clear increase of cutaneous oxygen supply by 212%. Erythrocyte flux in the deeper, dermal vessels and in the capillaries is enhanced by 66%.

The improvement of cutaneous oxygen supply and circulation lasts for more than one (1) hour after bathing, reaching values of 160% and 33%, respectively, at this time.

This result can be explained by the so-called depot effect of the two-phase bath, making possible a sustained and intensified action of the active ingredients on human skin. Due to the special galenical formulation of the product according to the invention, which contains the lipid-vesicle action complex, the active ingredients can form a layer on the skin while bathing (immediate effect) and effect a prolonged or protracted supply of the active ingredients to the skin for an extended period after bathing (depot effect). During this process, there is marked stimulation of cutaneous circulation, especially in the deeper dermal layers, and marked improvement of epidermal oxygen supply, which contributes to a general activation and mobilization of the body's own resistance.

Test 2

Ten volunteers with healthy skin were tested according to the above method, applying a preparation according to the invention containing 70% of fatty oil/apolar substances, 10% of oil-soluble surfactants, 5% of lecithin and rosemary oil, pine oil, ivy extract and vitamin E as active ingredients, according to Example 2.

Results

In healthy skin, the product according to the invention, as compared to blank water, effects a temporary, clear and sustained improvement of capillary and epidermal oxygen supply by 147% associated with an increase of dermal circulation by 41%.

The improvement of cutaneous oxygen supply and circulation continues for more than one (1) hour after bathing, reaching values of 123% and 7.3%, respectively, at this point in time. This can be explained by the so-called depot effect of the two-phase bath which ensures a protracted and intensified action of the active ingredients on human skin.

This test also confirms the high efficacy of the formulations according to the invention through the two-phase action, involving both immediate and deposit or depot effect, and the resulting long-lasting improvement of epidermal oxygen supply. This improves the skin's condition, its resistance, and its storage capacity for active ingredients over an extended period.

EXAMPLES 4–9

The following Compositions are prepared in essentially the manner described in Example 1 and found to be highly effective for their intended purpose, as already fully described for Examples 1–3, including a high degree of immediate dispersed vesicle formation in use as a bath or shower additive.

| Composition 4 | |
| --- | --- |
| Peanut oil | 65.0% |
| Isopropylpalmitate | 3.0% |
| Jojoba oil | 5.0% |
| PEG(4) laurylether | 13.0% |
| Lecithin | 0.5% |
| Ceramide | 2.0% |
| Rosemary oil | 6.0% |
| Pine oil | 5.0% |
| Tocopherol | 0.5% |
| Composition 5 | |
| Sesame oil | 50.0% |
| Octyldodecanol | 10.0% |
| Avocado oil | 5.0% |
| PEG(2)laurylether | 10.0% |
| PEG(7)glycerylcocoate | 5.0% |
| Lecithin | 2.0% |
| Sphingosine | 3.0% |
| Eucalyptus oil | 12.0% |
| Turpentine oil | 2.0% |
| Tocopherol | 1.0% |
| Composition 6 | |
| Medium-chain Triglycerides | 30.0% |
| Paraffin subliquidum | 30.0% |
| Isopropylmyristate | 5.0% |
| Almond oil | 10.0% |
| Mono-, Di- and Tri-(alkyltetra-glycolether)-O-phosphoric acid | 4.0% |
| PEG(4)laurylether | 8.0% |
| Cerebroside | 3.0% |
| Lecithin | 1.0% |
| Ivy extract | 4.0% |
| Calendula extract | 2.0% |
| Perfume oil | 2.0% |
| Tocopherol | 1.0% |
| Composition 7 | |
| Paraffin subliquidum | 21.0% |
| Soy oil | 30.0% |
| Olive oil | 5.0% |
| Octyldodecanol | 9.0% |
| Decyloleate | 5.0% |
| PEG(7)glycerylcocoate | 3.0% |
| PEG(2)laurylether | 12.0% |
| Sphingomyelin | 1.0% |
| PEG(2)stearylether | 2.0% |
| Lecithin | 0.5% |

| -continued | |
| --- | --- |
| Eucalyptus oil | 5.0% |
| Thyme oil | 1.5% |
| Rosemary oil | 4.0% |
| Tocopherol | 1.0% |
| Composition 8 (Shower composition) | |
| Soy oil | 40.0% |
| Medium-chain Triglycerides | 37.5% |
| Aerosil | 3.0% |
| Cocosfattyaciddiethanolamide | 5.0% |
| PEG(4)laurylether | 9.0% |
| Lecithin | 3.0% |
| Perfume oil | 2.5% |
| Composition 9 | |
| Paraffin subliquidum | 50.0% |
| Jojoba oil | 15.0% |
| Avocado oil | 9.0% |
| Oleyloleate | 5.0% |
| PEG(4)laurylether | 12.0% |
| PEG(2)cetylether | 2.0% |
| Lecithin | 1.0% |
| Cholesterol | 1.0% |
| Lavender oil | 2.5% |
| Citric oil | 1.0% |
| Camphor | 0.5% |

The replacement of lecithin in the foregoing examples by other suitable lipids, such as sphingomyelin, produces similarly good results, especially as to the vesicle-forming properties. Moreover, innumerable additional preparations in accord with the present invention, and having equivalent effectiveness, may be prepared and will immediately be apparent to one skilled in the art.

As will be seen from the foregoing Examples, in which compositions according to the present invention are prepared, and the foregoing clinical evaluations employing the same, the formulations or compositions of the present invention are useful per se as bath oil or shower compositions, whether complete or partial, and whether foot bath, hand bath, or for shampooing, either directly into the partial or complete bath, shower, or shampoo, or together with or as an additive for introduction into conventional bath, shower, or shampoo formulations, whether of oil, gel, or foam type, for the provision of vesicle-forming components therein and to improve the effectiveness and especially the sustained action thereof.

It is accordingly seen from the foregoing that the present invention provides novel bath or shower additive compositions or formulations comprising a fatty oil and/or a fatty or waxy apolar material, a vesicle-forming lipid, and an oil-soluble surfactant, together with an topically-active cosmetic ingredient, if desired, which formulation, upon introduction into, e.g., pouring into or simple admixture with, the bath water or liquid, spontaneously, i.e., automatically and immediately, forms dispersed vesicles or liposomes in the liquid, thereby providing a highly-effective and long-acting two-phase bath formulation, involving the immediate effect of providing a layer of the formulation and any active ingredient thereof upon the skin during the course of bathing or showering, as well as providing a prolonged or protracted supply of the formulation and any active ingredient contained therein after completion of bathing, thereby providing a valuable depot effect upon the skin for an extended period after bathing and involving a definite increase of cutaneous oxygen supply as well as erythrocyte flux in the deeper dermal vessels and in the capillaries, improving the skin condition, its resistance, and its storage capacity for active ingredients over an extended period and contributing to a general activation and mobilization of the body's own resistance, as well as a method for the preparation or formulation of such compositions.

It is to be understood that the present invention is not to be limited to the exact details of operation, or to the exact compounds, compositions, methods, procedures, or embodiments shown and described, as various modifications and equivalents will be apparent to one skilled in the art, wherefore the present invention is to be limited only by the full scope which can be legally accorded to the appended claims.

We claim:

1. A transparent anhydrous liquid balneological or cosmetic composition suitable as an additive for use in bathing or showering, having vesicle-forming properties, which spontaneously forms liposomes or vesicles immediately upon being admixed with water, and which produces an immediate and a delayed effect, consisting essentially of the following anhydrous ingredients:

20 to 90% by weight of the composition of at least one of a fatty oil and a fatty or waxy apolar substance, wherein the fatty oil is selected from the croup consisting of peanut, sesame, sunflower, wheat germ, soy, jojoba, castor, almond, mink, and olive oils, and wherein the fatty or waxy apolar substance is selected from the group consisting of paraffin oil, isopropyl myristate, isopropyl palmitate, triglycerides, isooctyl stearate, capryl/capric acid triglycerides, cetyl palmitate, and mixtures thereof, 2 to 50% by weight of the composition of at least one oil-soluble surfactant which is an oil-soluble water-dispersible tenside having an HLB value of 7 to 10, and which is selected from the group consisting of an oxyethylated lauryl ether having 1 to 4 EO units, polyoxyethylene (5)oleyl ether, polyoxyethylene(7) glyceryl cocoate, cocoa fatty acid diethanolamide, ethanolamide, mono or di or tri (alkyl tetraglycol ether)-ortho-phosphoric acid esters, polyoxyethylene glycerol trioleate, polmoxyethylene sorbitan tristearate- polyoxypropylene(15)-stearyl ether, and mixtures thereof, 0.1 to 20% by weight of the composition of at least one vesicle-forming lipid selected from the group consisting of an oxyethylated $C_{16}$–$C_{18}$ fatty alcohol having 1 to 4 ethylene oxide units and having an HLB value between 2 and 6 and a phospholipid selected from the group consisting of lecithin, phosphatidylcholine, -serine, or -diethanolamine or a mixture thereof, up to about 30% by weight of the composition of a cosmetically-active ingredient selected from the group consisting of essential oils, herbal extracts, and vitamins, and 0 to 10% by weight of the composition of a thickener.

2. A composition of claim 1, wherein the percentage of fatty oil and/or apolar substance is 50% to about 70%, the percentage of oil-soluble surfactant is 5% to 35%, and the percentage of vesicle-forming lipid is 0.5% to 5%, all by weight of total composition.

3. A composition of claim 2, wherein the percentage of oil-soluble surfactant is 10% to 20% by weight of the composition.

4. A composition of claim 1, wherein the vesicle-forming lipid is a phospholipid and the HLB value of the oil-soluble surfactant is about 8.

5. A composition of claim 3, wherein the oil-soluble surfactant is an oxyethylated lauryl ether having 1 to 4 EO units.

6. A composition of claim 1 wherein the amount of cosmetically-active ingredient is 5 to 15% by weight of the composition.

7. A composition of claim 1, wherein the thickener is selected from the group consisting of aerosil and aluminum or magnesium stearate.

8. A composition of claim 1 wherein the oil and/or apolar substance comprises at least soya oil and/or jojoba oil, wherein the oil-soluble surfactant is an oxyethylated lauryl ether having 1 to 4 EO units, and wherein the vesicle-forming lipid is at least 3% by weight of the total composition of lecithin.

9. A composition of claim 3 wherein the oil and/or apolar substance comprises at least soya oil and/or jojoba oil, wherein the oil-soluble surfactant is an oxyethylated lauryl ether having 1 to 4 EO units, and wherein the vesicle-forming lipid is at least 3% by weight of the total composition of lecithin.

10. A method for the production of a transparent anhydrous liquid bath or shower additive composition, which spontaneously forms dispersed liposomes or vesicles immediately upon being admixed with water, and which produces an immediate and a delayed effect, which comprises the step of admixing together at a temperature between about 20° C. and 70° C. the following ingredients:

20 to 90% by weight of the composition of at least one of a fatty oil and a fatty or waxy apolar substance, wherein the fatty oil is selected from the group consisting of peanut, sesame, sunflower, wheat germ, soy, jojoba, castor, almond, mink, and olive oils, and wherein the fatty or waxy apolar substance is selected from the group consisting of paraffin oil, isopropyl myristate, isopropyl palmitate, triglycerides, isooctyl stearate, capryl/capric acid triglycerides, cetyl palmitate, and mixtures thereof, 2 to 50% by weight of the composition of at least one oil-soluble surfactant which is an oil-soluble water-dispersible tenside having an HLB value of 7 to 10, and which is selected from the group consisting of an oxyethylated lauryl ether having 1 to 4 EO units, polyoxyethylene (5)oleyl ether, polyoxyethylene(7) glyceryl cocoate, cocoa fatty acid diethanolamide, ethanolamide, mono or di or tri (alkyl tetraglycol ether)-ortho-phosphoric acid esters, polyoxyethylene glycerol trioleate, polyoxyethylene sorbitan tristearate, polyoxypropylene(15)-stearyl ether, and mixtures thereof, 0.1 to 20% by weight of the composition of at least one vesicle-forming lipid selected from the group consisting of an oxyethylated $C_{16}$–$C_{18}$ fatty alcohol having 1 to 4 ethylene oxide units and having an HLB value between 2 and 6 and a phospholipid selected from the group consisting of lecithin, phosphatidylcholine, -serine, or -diethanolamine, or a mixture thereof, up to about 30% by weight of the composition of a cosmetically-active ingredient selected from the group consisting of essential oils, herbal extracts, and vitamins, and 0 to 10% by weight of the composition of a thickener.

11. A method of claim 10, wherein the percentage of fatty oil and/or apolar substance is 50% to about 70%, the percentage of oil-soluble surfactant is 5% to 1%, and the percentage of vesicle-forming lipid is 0.5% to 5%, all by weight of total composition.

12. A method of claim 11, wherein the percentage of oil-soluble surfactant is 10% to 20% by weight of the composition.

13. A method of Claim 10, wherein the vesicle-forming lipid is a phospholipid and the HLB value of the oil-soluble surfactant is about 8.

14. A method of claim 10, wherein the oil-soluble surfactant is an oxyethylated lauryl ether having 1 to 4 EO units.

15. A method of claim 10 wherein the amount of cosmetically-active ingredient is 5 to 15% by weight of the composition.

16. A method of claim 10, wherein the thickener is selected from the group consisting of aerosil and aluminum or magnesium stearate.

17. A method of claim 10, wherein the oil and/or apolar substance comprises at least soya oil and/or jojoba oil, wherein the oil-soluble surfactant is an oxyethylated lauryl ether having 1 to 4 EO units, and wherein the vesicle-forming lipid is at least 3% by weight of the total composition of lecithin.

18. A method of claim 12 wherein the oil and/or apolar substance comprises at least soya oil and/or jojoba oil, wherein the oil-soluble surfactant is an oxyethylated lauryl ether having 1 to 4 EO units, and wherein the vesicle-forming lipid is at least 3% by weight of the total composition of lecithin.

* * * * *

UNITED STATES PATENT AND TRADEMARK OFFICE
CERTIFICATE OF CORRECTION

PATENT NO. : 5,766,628
DATED : June 16, 1998
INVENTOR(S) : E. Nurnberg, T. Gassenmeier, R. D. Beutler, J. Ebinger It is certified that error appears in the above-indentified patent and that said Letters Patent is hereby corrected as shown below:

Column 6, line 17: "as lipo-somes" should read
    -- as liposomes --.

Column 6, line 20: "influenc- ing" should read
    -- influencing --.

Column 12, line 20: "2.0%" should read -- 2.5% --.

Column 12, line 24: "1.0%" should read -- 1.5% --.

Column 14, line 65: "5% to 1%," should read
    -- 5% to 35% --.

Signed and Sealed this

Eighteenth Day of August, 1998

Attest:

BRUCE LEHMAN

Attesting Officer     Commissioner of Patents and Trademarks